United States Patent [19]

Dantanarayana

[11] Patent Number: 5,336,246
[45] Date of Patent: Aug. 9, 1994

[54] LEAD CONNECTOR ASSEMBLY FOR MEDICAL DEVICE AND METHOD OF ASSEMBLY

[75] Inventor: Muditha Dantanarayana, North Ryde, Australia

[73] Assignee: Telectronics Pacing Systems, Inc., Englewood, Colo.

[21] Appl. No.: 81,583

[22] Filed: Jun. 23, 1993

[51] Int. Cl.⁵ .................................... A61N 1/375
[52] U.S. Cl. ................................................ 607/37
[58] Field of Search ............................ 607/36, 37

[56] References Cited

U.S. PATENT DOCUMENTS

| | | | |
|---|---|---|---|
| 3,683,932 | 8/1972 | Cole | 607/37 |
| 4,142,532 | 3/1979 | Ware | 607/37 |
| 4,182,345 | 1/1980 | Grese | 607/37 |
| 4,226,244 | 10/1980 | Coury et al. | 607/37 |
| 4,262,673 | 4/1981 | Kinney et al. | 607/37 |
| 4,715,380 | 12/1987 | Harris | 128/419 P |
| 4,898,173 | 2/1990 | Daglow et al. | 607/37 |
| 4,934,366 | 6/1990 | Truex et al. | 128/419 P |
| 4,995,389 | 2/1991 | Harris | 128/419 P |

*Primary Examiner*—William E. Kamm
*Attorney, Agent, or Firm*—Gottlieb, Rackman & Reisman

[57] ABSTRACT

An implantable electrical device, including a sealed case and a connector assembly, and a method for making the same are disclosed. The sealed case has electrical circuitry therein and has at least one insulated electrical-feed-through coupled to the circuitry. The feed-through member extends from the interior of the case to the exterior of the case and includes an external electrical terminal. The connector assembly has an apertured housing adapted to receive the proximal end portion of an electrical lead in sealing engagement with the housing. The connector assembly also has at least one electrical contact therein adapted to be engaged by a terminal of the electrical lead, and at least one insulated feed-through member coupled to the contact and extending from the interior of the assembly to the exterior of the assembly, the feed-through member including an external electrical terminal. The feed-through members of the sealed case and the connector assembly interconnect the connector assembly and the case together in such a manner that the external terminal of the feed-through member on the assembly electrically contacts the external terminal of the feed-through member on the case. The sealed case and the connector assembly are separately fabricated and, as a final step in the manufacture of the device, they are adhesively bonded together, with the external terminal of each in electrical contact with the external terminal of the other.

10 Claims, 3 Drawing Sheets

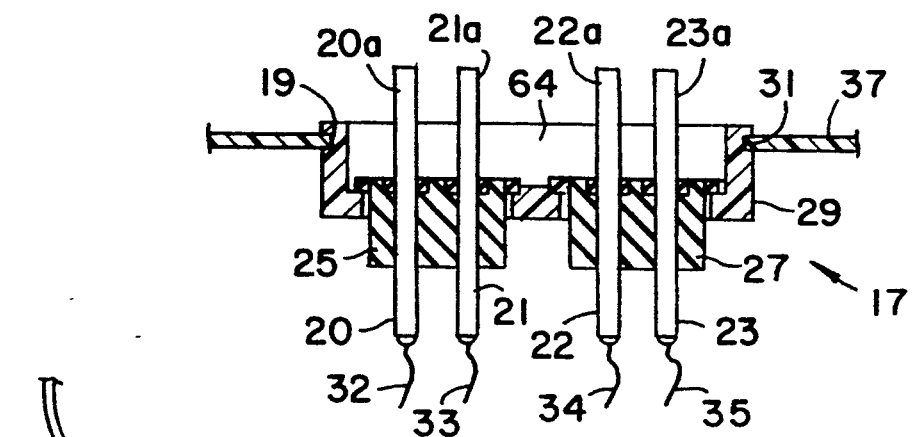
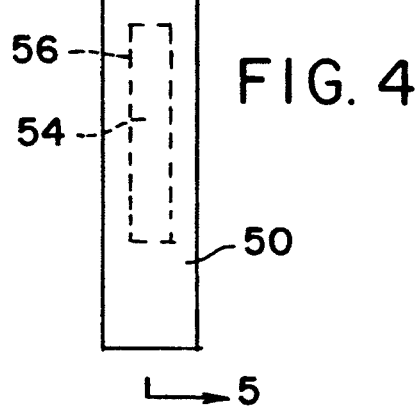
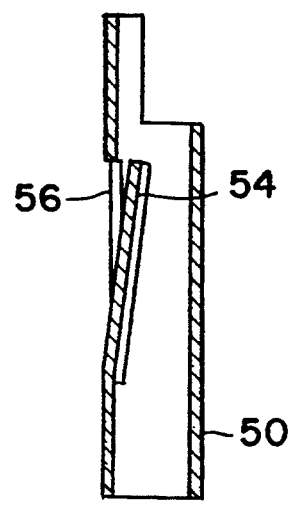
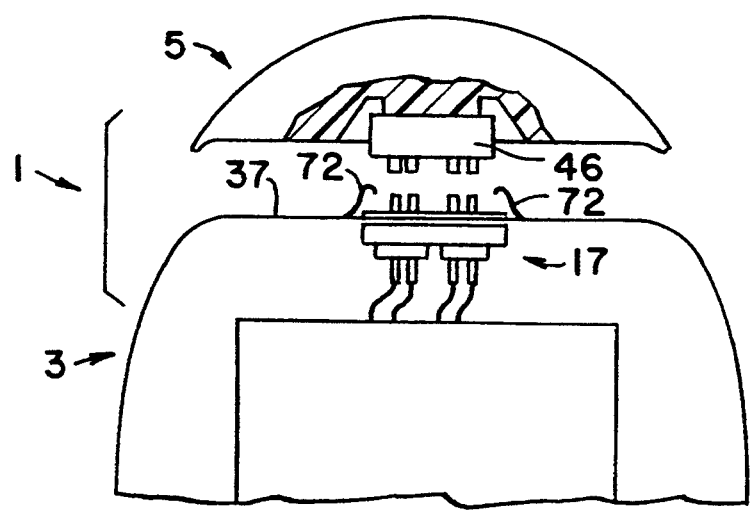

LEAD CONNECTOR ASSEMBLY FOR MEDICAL DEVICE AND METHOD OF ASSEMBLY

BACKGROUND OF THE INVENTION

This invention relates to an implantable electrical device having a lead connector assembly attached thereto and, more particularly, to implantable pacemaker/cardioverter/defibrillator devices having electrode-lead-receiving connector assemblies that are manufactured separately from and thereafter connected to the remainders of the devices.

The invention will be described herein in connection with its use in a pacemaker system. However, it will be apparent to those skilled in the art that the invention has broader applicability to other implantable electrical devices in which a connector assembly is employed to connect electrical leads to electrical circuits.

The operation of an implantable heart pacemaker requires the transmission to the pacemaker of low level electrical signals generated by the heart, as well as the transmission to the heart of pacing voltages generated by the pacemaker. The pacer generally comprises a metal case within which electrical circuits are carried, and a connector assembly having terminal jacks therein which are connected to the electrical circuits within the metal case and into which terminal pins on the proximal end of an electrode lead are received.

Conventionally, connector assemblies are fabricated and installed upon metal pacer cans after the internal electrical circuits of the cans have been installed and the manufacturing of the can is otherwise completed. In adding the connector assembly to the completed can, the terminal jacks of the connector assembly are electrically joined to feed-throughs which extend from within the can to the area of the terminal jacks in the connector assembly. This type of prior art pacemaker system may be seen in U.S. Pat. Nos. 4,715,380 and 4,995,389 to D. L. Harris.

One problem extant with pacemaker systems of the type shown in the Harris patents is that the connector assembly thereof cannot be constructed without first providing the fully finished pacemaker can. Accordingly, the connector assemblies cannot be stocked. Also, if the feed-throughs are not properly electrically connected to the terminal jacks, or if one of the wires connecting the feed-throughs to the terminal jacks breaks, the effort and expense encountered in manufacturing the pacemaker can is wasted since the feed-throughs, the can, the connector assembly and the electrical circuits within the can will all be rejected. This is a costly process which would be desirable to avoid.

Another problem extant in prior art pacemaker systems may be seen in U.S. Pat. No. 4,934,366 to D. E. Truex and W. H. Stutz, Jr. In this case the electrode-lead-receiving terminal jacks are incorporated within a barrel assembly that is, itself, positioned within the metallic case of the pacemaker so that the feed-throughs employed in the Harris type pacemaker systems are eliminated. One disadvantage resulting from this type of pacemaker system is that the overall size of the pacemaker is larger than it would be if the Harris type system is employed. Moreover, at present there is an increasing demand for smaller units having a larger number of electrode lead connectors therein. This makes the Truex and Stutz type of pacing system impractical.

It is, therefore, a primary object of the present invention to provide for improved connections between the connector assemblies and the cases of pacemaker systems.

It is a further object of the present invention to accommodate a large number of lead connectors in a small connector assembly.

It is another object of the present invention to facilitate the separate manufacture of pacemaker case units and connector assembly units, each of which units are provided with cooperating plug-in features that allow them to be assembled together upon completion of the manufacture of such units.

It is yet another object of the present invention to provide for improved attachment of and electrical connections between sealed connector assemblies and sealed electrical-circuit-containing cases of implantable electrical devices.

Further objects and advantages of this invention will become apparent as the following description proceeds.

SUMMARY OF THE INVENTION

Briefly stated, and in accordance with one embodiment of the present invention, there is provided an implantable electrical device which comprises a sealed case having electrical circuitry therein and having at least one insulated electrical-feed-through member coupled to the circuitry and extending from the interior of the case to the exterior of the case, the feed-through member including an electrical terminal carried externally of the case. The device also includes a connector assembly having an apertured housing adapted to receive a proximal, electrical-terminal-carrying, end portion of an electrical lead in sealing engagement with the housing, whereby the interior of the connector assembly is sealed from the exterior thereof when in engagement with the electrical lead, the connector assembly having at least one electrical contact therein adapted to be engaged by a terminal of the electrical lead and having at least one insulated feed-through member coupled to the contact and extending from the interior of the assembly to the exterior of the assembly, the feed-through member including an electrical terminal carried externally of the assembly. The device further includes means for fastening the case and the connector assembly together in such a manner that the external terminal of the feed-through member on the assembly electrically contacts the external terminal of the feed-through member on the case.

In accordance with another aspect of the invention, there is provided a method of making an electrical device, the device including a sealed case and a connector assembly. The method includes the step of providing a sealed case having electrical circuitry therein and having at least one insulated electrical-feed-through member coupled to the circuitry and extending from the interior of the case, the feed-thorough member including an electrical terminal carried externally of the case. The method also includes the step of providing a connector assembly having an appertured housing adapted to receive a proximal, electrical-terminal-carrying end portion of an electrical lead in sealing engagement with the housing, whereby the interior of the connector assembly is sealed from the exterior thereof when in engagement with the electrical lead, the connector assembly having at least one electrical contact therein adapted to be engaged by a terminal of the electrical lead and having at least one insulated feed-through member coupled to the contact and extending from the interior of the assembly to the exterior of the assembly, the feed-through member including an electrical terminal carried externally of the assembly. The method further includes the step of fastening the connector assembly and the sealed case to one another in such a manner that the external terminal of the feed-through member on the assembly electrically contacts the external terminal of the feed through member on the case.

BRIEF DESCRIPTION OF THE DRAWINGS

While the specification concludes with claims particularly pointing out and distinctly claiming the subject matter of the invention, it is believed that the invention will be better understood from the following description, taken in conjunction with the accompanying drawings, in which:

FIG. 3 is an enlarged sectional elevation view of a feed-through member and a portion of the sealed case of FIG. 2, showing electrical terminals that extend through the feed-through member to a position outside of the sealed case;

FIG. 4 is an enlarged elevation view of an electrical terminal that extends through a feed-through member in the connector assembly of FIG. 2;

FIG. 5 is a sectional elevation view of the electrical terminal of FIG. 4, taken along the line 5—5 of FIG. 4;

DETAILED DESCRIPTION OF THE PREFERRED EMBODIMENT

Figure 1:
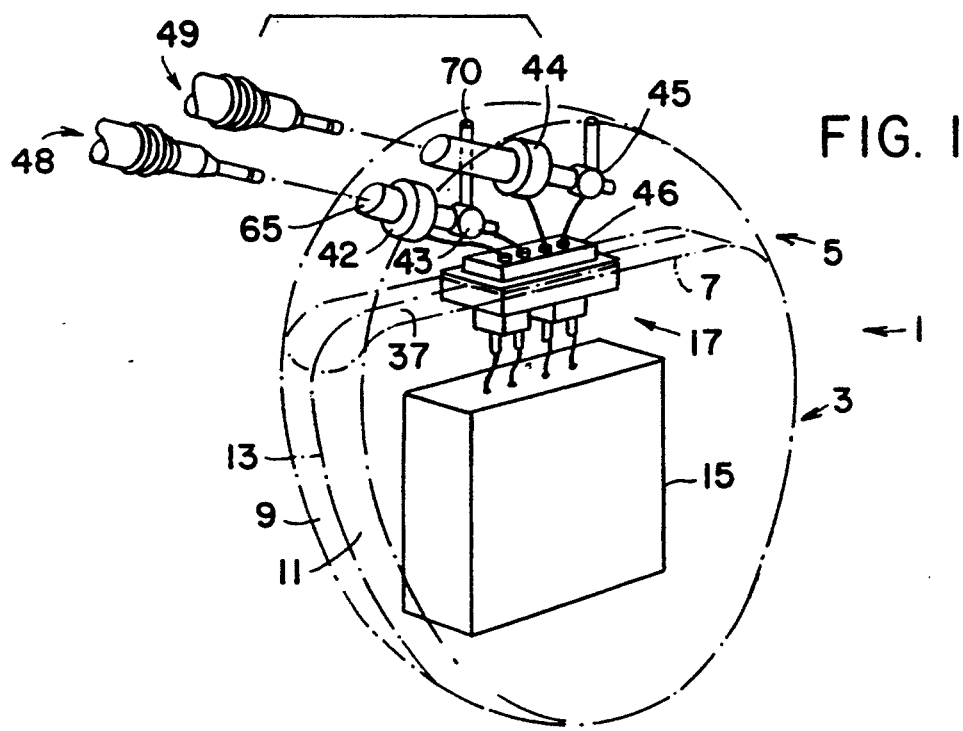
FIG. 1 is a schematic perspective view of a pacemaker/cardioverter/defibrillator device in accordance with the present invention.

The present invention will now be described with reference to the drawings, in which the same reference characters 25 are used to designate like elements in the various view.

Referring to FIG. 1, a pacemaker/cardioverter/defibrillator device is shown generally at 1 in a fully assembled condition. The device 1 includes a sealed case, shown generally at 3, and a connector assembly, shown generally at 5, which are adhesively bonded together at their interface 7 by, for example, a Silastic ® adhesive rubber made by Dow Corning Corporation, 2200 West Salzburg Road, Midland, Mich. 48640. The connector assembly 5 and the sealed case 3 are made in two separate processes and, at the final stage, the connector assembly 5 is plugged into the case 3 and adhered thereto.

Figure 2:
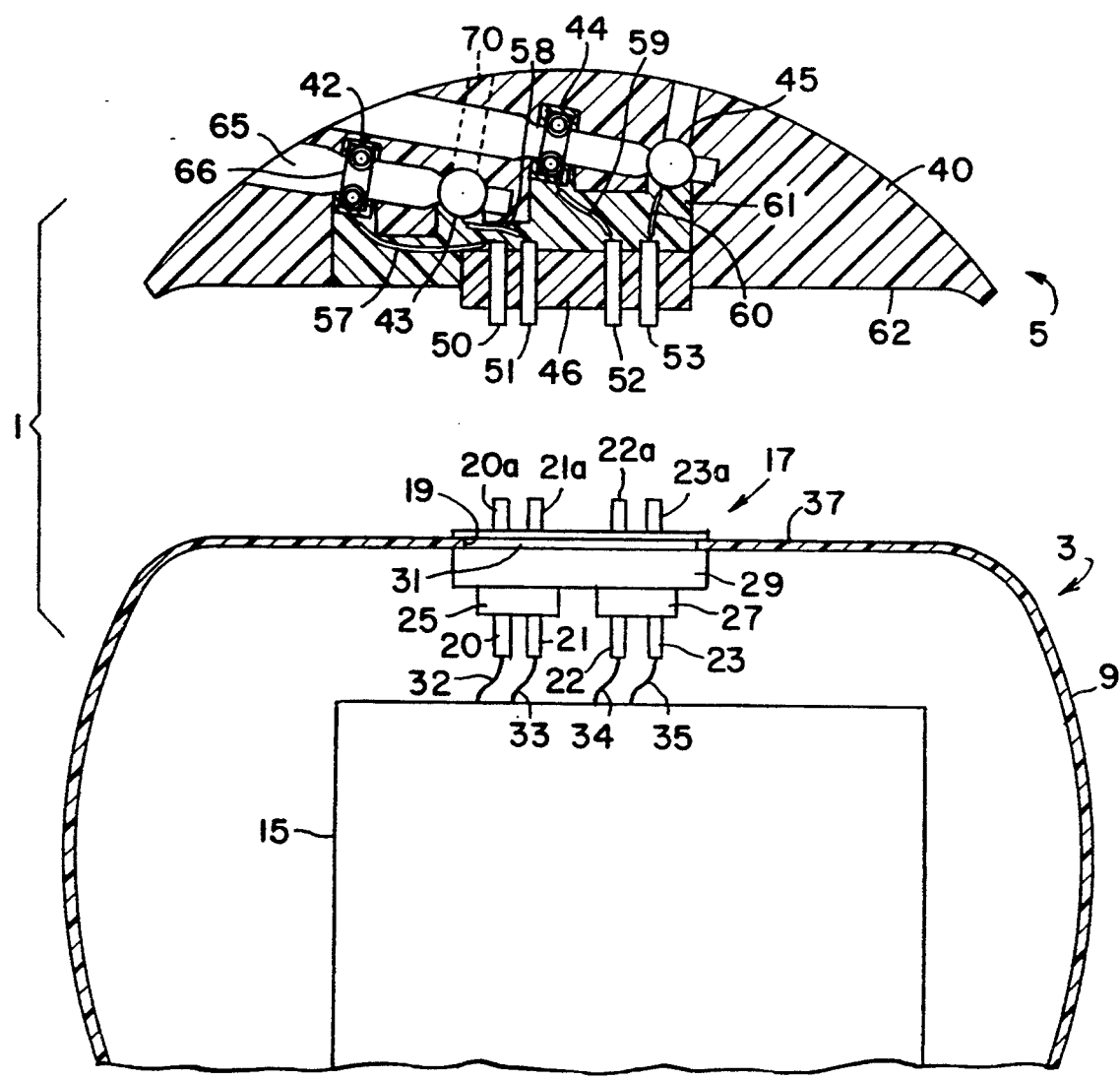
FIG. 2 is an enlarged elevation view, with parts cut away for clarity, of the device of FIG. 1, showing the separate connector assembly and sealed case thereof prior to their being fastened together.

Referring to FIGS. 1–3, together, the sealed case 3 will now be considered in greater detail. The case 3 is comprised of two cup-shaped half-case members 9 and 11 which are joined together along a seam 13 to form the case 3. Prior to the two half-case members being welded to one another along seam 13, an electronics module or package 15, containing the pacemaker/cardioverter/defibrillator circuitry, is fixedly fastened within one of the half-case members, for example member 9, by an adhesive or mounting means (not shown), and a feed-through assembly or member, shown generally at 17, is positioned within a cut out portion 19 of the half-case member 9 and adhesively sealed thereto.

As shown most clearly in FIG. 3, the feed-through assembly 17 includes a plurality of metallic, conductive pins 20–23 which are bonded (e.g., by brazing) to ceramic blocks 25 and 27 which, in turn, are similarly bonded to a metal flange 29. The flange 29 is provided with a groove 31 about its periphery that mates both with the cut out portion 19 of the half-case member 9 and with a similar cut out portion (not shown) in the half-case member 11.

In assembling the sealed case 3, feed-through assembly 17 is initially positioned within the cut out portion 19 of half-case member 9 and the flange 29 thereof is peripherally welded to the half-case member 9 adjacent to the interface at which the cut out portion 19 mates with the groove 31. As indicated earlier, electronics module 15 is fixedly mounted in the half-case member 9 and, referring to FIG. 2, is electrically connected to the metallic conductive pins 20–23 by respective wires 32–35. When the module 15 and the feed-through assembly 17 have been mounted on the half-case member 9, and the wires 32–35 have been electrically connected to the pins 20–23, the half-case member 11 is positioned onto the half-case member 9 so that its cut out portion corresponding to cut out portion 19 engages the groove 31 of feed-through assembly 17. At this point the two half-case members 9 and 11 are circumferentially welded along the seam 13 and the cut out portion of half-case member 11 is welded to the flange 29, adjacent the groove 31, so that the case 3 is hermetically sealed relative to ambient conditions outside of the case, and so that electrical terminal portions 20a–23a of pins 20–23 extend outwardly of the sealed case 3 and outwardly of a generally planar end surface 37 formed by the joining of the two half-case members 9 and 11 to one another.

Referring now to FIGS. 1, 2 and 4–6, together, the connector assembly 5 of the device 1 will now be considered in greater detail. The connector assembly 5 comprises a pre-cast epoxy shell 40 having internal cavities to accommodate terminal blocks, shown generally at 42–45, a socket housing 46 and electrode leads from the patient, shown generally at 48 and 49. The epoxy shell is made by casting epoxy in a rubber mold. The internal cavities and the electrode lead cavities are formed by using a brass core and core pins during the molding operation, while the rubber mold forms the outer shape of the epoxy shell.

Socket housing 46 is a sub-assembly of the connector assembly 5. The socket housing 46 comprises a rectangular epoxy block having through holes therein which accommodate respective metallic conductive electrical socket terminals or members 50–53, which, when the connector assembly 5 and case 3 are assembled together are in alignment with and receive the respective external electrical pin terminal portions 20a–23a of the sealed case 3.

As shown more clearly in FIGS. 4 and 5, wherein the socket terminal member 50 is shown enlarged and in greater detail, the socket terminal members 50–53 are generally tubular in shape and are provided with integral leaf springs 54 which are formed by cutting a U-shaped slot 56 in the tube and pressing the leaf spring 54 radially inwardly of the tube. The socket terminals 50–53 are inserted into the housing 46, and respective insulated connecting wires 57–60 are spot welded thereto.

The terminal blocks 42–45 are then placed and aligned in their respective cavities in connector assembly 5. The socket housing 46 is also placed inside the connector assembly 5 and the ends of the connecting wires 57–60 remote from the socket terminals 50–53 are welded to the respective terminal blocks 42–45. At this point the socket housing 46 and the terminal blocks 42–45 are aligned relative to the connector assembly shell 40 and the shell is filled with epoxy 61 (FIG. 6) to fill in the gaps therein, completing the processing of forming the connector assembly 5.

The sealed case 3 and the connector assembly 5 may be separately tested and stored independently of one another for subsequent final assembly to one another. Final assembly is accomplished by applying an adhesive bonding agent either to the end surface 37 surrounding the feed-through assembly 17 of case 3, or to a corresponding end surface 62 (FIG. 2) surrounding the socket housing 46 of connector assembly 5. The end surfaces 37 and 62 are complementary to one another to facilitate the bonding of the surfaces 37 and 62 to one another in a manner which seals the electrical terminals of feed-through assembly 17 and socket housing 46 from ambient conditions external to the device 1. In connection with adhesively bonding the surfaces 37 and 62 to one another, the terminal pins 20a–23a are plugged into the sockets 50–53 when the connector assembly 5 and sealed case 3 are brought into contact with one another. Also, the housing 46 on connector assembly 5 fits into and mates with a well 64 (FIG. 3), formed in the feed-through assembly 17 by the flange 29, to allow the two surfaces 37 and 62 to come into contact with one another, and to facilitate achieving good metal to metal electrical contact between the pin terminals 20a–23a and the socket terminals 50–53. Thus, when the connector assembly 5 is plugged into the case 3, the socket terminals 50–53 of the connector assembly provide positive electrical connection with the feed-through pins 20–23 of the case and, thus, electrical signals are conducted between the electronics module 15 of the case 3 and the terminal blocks 42–45 of the connector assembly 5.

Figure 6:
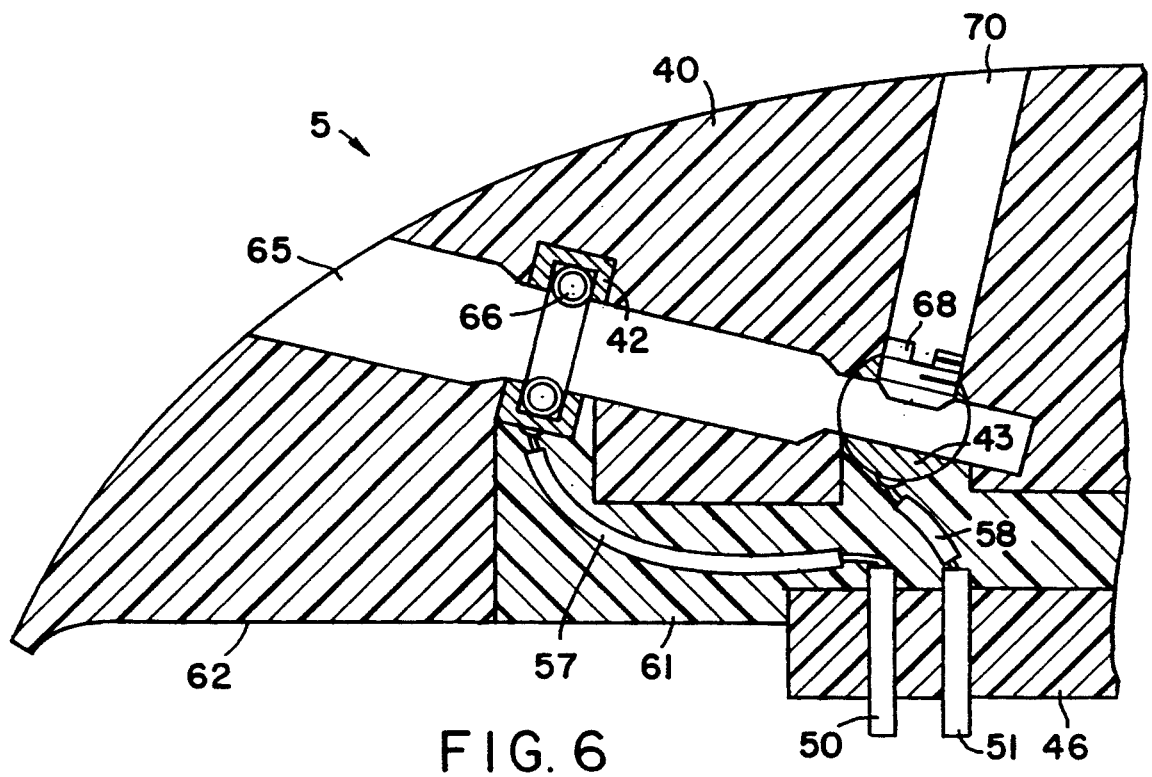
FIG. 6 is an enlarged sectional elevation view of a portion of the connector assembly of FIG. 2, showing an apertured housing thereof that is adapted to receive an electrical-terminal-carrying end portion of an electrical lead therein; and, FIG. 7 is a view similar to FIG. 2, showing an alternate embodiment of the device.

Referring to FIG. 6, detailed cross sections are shown therein of two of the terminal blocks, blocks 42 and 43. When the proximal portion of the electrode lead 48 (FIG. 1) from a patient is fully inserted into a complementary cavity 65 in the connector assembly 5, the electrical terminals of the lead contact the corresponding terminal blocks 42 and 43 and provide electrical interconnection between the electrode lead 48 and the device 1. The terminal block 42 comprises a conductive metal member which includes a circumferentially arranged spring 66 therein that is in electrical contact with terminal block 42. Terminal block 42, as indicated earlier, is connected to one end of the insulated wire 57, the other end of which is coupled to the electronic module 15 via socket terminal 50, pin terminal 20, and wire 32. Similarly, the terminal block 43 provides electrical contact with another terminal on the lead 48 by means of a conductive metal screw 68 which threadedly engages the terminal block 43 and is screwed tightly against the terminal on the lead, in accordance with conventional practice. The screw 68 is accessed by the physician via a cavity 70 at the time of installation of the device 1, and the cavity 70 is sealed by a septum (not shown) which is placed therein in order to prevent body fluids from seeping through the cavity 70, also in accordance with conventional practice. The terminal block 43 is a conductive metal member, and it is electrically coupled to the electronics module 15 by means of the insulated wire 58 welded thereto and by other heretofore described components. The terminal blocks 44 and 45 (FIG. 2) are constructed and arranged in manners similar to respective terminal blocks 42 and 43 to receive, and electrically couple to the electronic module, a second electrode lead 49 (FIG. 1).

Referring to FIG. 7, an alternative embodiment for holding the connector assembly 5 to the sealed case 3 has there been shown. In this embodiment, leaf springs 72 are provided which are welded to the planar surface 37 of the sealed case 3. Leaf springs 72 engage the upper surface of the socket housing 46, locking the housing 46 to the feed-through assembly 17 and providing additional mechanical strength for the joint between the sealed case 3 and the connector assembly 5.

It will be apparent from the foregoing discussion that the present invention provides for improved connections between the connector assemblies and the cases of pacemaker systems. The invention accommodates a large number of lead connectors in a small connector assembly, and facilitates the separate manufacture of pacemaker case units and connector assembly units, each of which units are provided with cooperating plug-in features that allow them to be assembled together upon completion of the manufacture of such units. The invention thus provides for improved attachment of and electrical connections between sealed connector assemblies and sealed electrical-circuit-containing cases of implantable electrical devices.

While particular embodiments of this invention have been shown and described, it will be obvious to those skilled in the art that various other changes and modifications may be made without departing from this invention in its broader aspects, and it is, therefore, aimed in the appended claims to cover all such changes and modifications as fall within the true spirit and scope of this invention.

What is claimed is:

1. An implantable electrical device comprising:
   a sealed case having electrical circuitry therein and having at least one insulated electrical-feed-through member coupled to said circuitry and extending from the interior of said case to the exterior of said case, said feed-through member including an electrical terminal carried externally of said case;
   a connector assembly having an apertured housing adapted to receive a proximal, electrical-terminal-carrying, end portion of an electrical lead in sealing engagement with said housing, whereby the interior of said connector assembly is sealed from the exterior thereof when in engagement with the electrical lead, said connector assembly having at least one electrical contact therein adapted to be engaged by a terminal of the electrical lead and having at least one insulated feed-through member coupled to said contact and extending from the interior of said assembly to the exterior of said assembly, said feed-through member including an electrical terminal carried externally of said assembly; and
   means for fastening said connector assembly and said sealed case together in such a manner that the external terminal of the feed-through member on the assembly electrically contacts the external terminal of the feed-through member on the case.

2. A device according to claim 1, wherein said fastening means comprises an adhesive that bonds said connector assembly to said sealed case.

3. A device according to claim 1, wherein said sealed case and said connector assembly each include an outer end surface that is complimentary to the outer end surface of the other, said end surfaces being adapted to abut one another and having the respective external terminals of said sealed case and said connector assembly positioned generally centrally thereof, and wherein said fastening means includes an adhesive positioned on at least a peripheral portion of at least one of said end surfaces that surrounds a respective external terminal, said adhesive serving to bond said end surfaces to one another to thereby join said sealed case to said connector assembly and seal said electrical terminals from ambient conditions that are external of said sealed case and said connector assembly.

4. A device according to claim 3, wherein the respective feed-through members of said sealed case and said connector assembly extend through the respective end surfaces of said sealed case and said connector assembly, are bonded thereto, and are generally centrally positioned therein.

5. A device according to claim 4, wherein one of said feed-through members comprises a plug member and the other of said feed-through members comprises a socket member, and wherein said plug member is inserted into said socket member when said sealed case and said connector assembly are fastened to one another.

6. A method of making an electrical device, said device including a sealed case and a connector assembly, comprising the steps of:

providing a sealed case having electrical circuitry therein and having at least one insulated electrical feed-through member coupled to said circuitry and extending from the interior of said case to the exterior of said case, said feed-through member including an electrical terminal carried externally of said case;

providing a connector assembly having an apertured housing adapted to receive a proximal, electrical-terminal-carrying end portion of an electrical lead in sealing engagement with said housing, whereby the interior of the connector assembly is sealed from the exterior thereof when in engagement with the electrical lead, said connector assembly having at least one electrical contact therein adapted to be engaged by a terminal of the electrical lead and having at least one feed-through member coupled to said contact and extending from the interior of said assembly to the exterior of said assembly, said feed-through member including an electrical terminal carried externally of said assembly; and, fastening said connector assembly and said sealed case to one another in such a manner that the external terminal of the feed-through member on the .assembly electrically contacts the external terminal of the feed-through member on the case.

7. A method according to claim 6, wherein said fastening step includes the sub-step of adhesively bonding said sealed case to said connector assembly.

8. A method according to claim 6, wherein said sealed case and said connector assembly each include an outer end surface that is complimentary to the outer end surface of the other, said surfaces being adapted to abut one another and having the respective external terminals of said sealed case and said connector assembly positioned generally centrally thereof, and wherein said fastening step includes the sub-steps of applying an adhesive to at least a peripheral portion of at least one of said end surfaces that surrounds the respective external terminal, and bonding said end surfaces to one another to join said sealed case and said connector assembly to one another and to seal said electrical terminals from ambient conditions that are external of said sealed case and said connector assembly.

9. A method according to claim 8, wherein the respective feed-through members of said sealed case and said connector assembly extend through the respective end surfaces of said sealed case and said connector assembly and are generally centrally positioned therein, and wherein said sealed case providing step includes a sub-step of bonding the feed-through member of said case to the end surface of said case.

10. A method according to claim 9, wherein one of said feed-through members comprises a plug member and the other of said feed-through members comprises a socket member, and wherein said fastening step includes a further sub-step, following said adhesive applying step, of inserting said plug member into said socket member to cause said external terminals to electrically contact one another.

* * * * *